US008831741B2

(12) United States Patent
Griswold

(10) Patent No.: US 8,831,741 B2
(45) Date of Patent: Sep. 9, 2014

(54) CATHETER WITH DEFLECTABLE CAP

(75) Inventor: Erik Griswold, Penngrove, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 848 days.

(21) Appl. No.: 13/047,525

(22) Filed: Mar. 14, 2011

(65) Prior Publication Data
US 2012/0239002 A1 Sep. 20, 2012

(51) Int. Cl.
*A61N 1/05* (2006.01)
*A61M 39/24* (2006.01)
*A61M 25/00* (2006.01)

(52) U.S. Cl.
CPC ... *A61M 25/0074* (2013.01); *A61M 2025/0079* (2013.01)
USPC ............ 607/116; 604/508; 604/510

(58) Field of Classification Search
USPC ........... 607/115, 116; 623/1.12; 604/66, 508, 604/510
See application file for complete search history.

(56) References Cited

U.S. PATENT DOCUMENTS

| 6,254,633 | B1 | 7/2001 | Pinchuk |
| 6,322,586 | B1 | 11/2001 | Monroe |
| 2003/0004537 | A1 | 1/2003 | Boyle |
| 2005/0215945 | A1* | 9/2005 | Harris et al. ................ 604/66 |
| 2006/0099238 | A1 | 5/2006 | Khosravi |
| 2007/0233224 | A1* | 10/2007 | Leynov et al. ............. 623/1.12 |
| 2009/0082828 | A1 | 3/2009 | Ostroff |

* cited by examiner

*Primary Examiner* — Christopher D Koharski
*Assistant Examiner* — Michael Carey

(57) ABSTRACT

A catheter system for delivery of a medical implant, the system including a cap removably covering an open distal end of a catheter. An elongate actuator wire is fixedly attached to the cap, extends through a lumen of the catheter, and has a distal region that can assume a pre-formed shape when unconstrained by the catheter lumen. The pre-formed shape of the wire distal region defines a bend adapted to laterally deflect the cap from the catheter distal end when assuming the pre-formed shape. At least a portion of the lumen adjacent the catheter distal end is sized and shaped to slidably receive the medical implant alongside the actuator wire. A push rod extends through the catheter lumen for ejecting the medical implant from the catheter distal end. Methods of using the invention are also disclosed.

17 Claims, 3 Drawing Sheets

CATHETER WITH DEFLECTABLE CAP

TECHNICAL FIELD

This invention relates generally a catheter system for delivering an implantable cardiovascular treatment device. A cap for leading the system through the vasculature is deflectable from a catheter open distal end.

BACKGROUND OF THE INVENTION

Catheters are commonly used in vascular procedures. The catheter is threaded through the vasculature to a treatment site and treatment is delivered to or applied at the site. The treatment can take many forms, but a common treatment includes delivery of an implantable stent that may be collapsed or compressed to a low profile during delivery. Other catheterization treatments include the delivery of non-collapsible devices that have a relatively large transverse cross section. In certain of these non-collapsible implant devices it is undesirable to provide a passage through the device to accommodate medical guidewires or the like to assist in delivery of the device. For example, it is undesirable to design a battery for a wireless implantable pacemaker wherein the battery has a through hole to accommodate a guidewire.

Implantable devices that cannot be tracked concentrically over a guidewire are typically carried inside a sheath or catheter and are pushed out of the catheter open distal end by an elongate element such as a flexible rod slidably disposed in the lumen of the catheter. Especially in delivery systems where the catheter open end is necessarily large enough to accommodate the profile of the non-collapsible implant being delivered, the distal end of the catheter distal end can get caught on vascular tissue or can be misdirected into branch vessels, resulting in undesirably extending the clinical time required to deliver the implant. Therefore, it would be desirable to provide an implant delivery system that overcomes the aforementioned and other disadvantages.

SUMMARY OF THE INVENTION

One aspect of the present invention is a catheter system that includes an elongate catheter having a lumen terminating at an open distal end. A cap is removably mounted covering the catheter distal end and having a rounded distal tip for guiding the catheter system through the patient's vasculature. An elongate actuator wire is fixedly attached to the cap, extends through the lumen of the catheter, and has a distal region that can assume a pre-formed shape when unconstrained by the catheter lumen. The pre-formed shape of the wire distal region defines a bend adapted to laterally displace the cap from the catheter distal end when assuming the pre-formed shape. At least a portion of the lumen adjacent the catheter distal end is adapted to slidably receive the medical implant alongside the actuator wire. A push rod extends through the catheter lumen for ejecting the medical implant from the catheter distal end.

A method for delivering an implantable device that cannot be tracked concentrically over a guidewire includes a catheter system that has a lumen terminating at an open distal end of a catheter. A cap is removably mounted covering the catheter distal end and has a rounded distal end. An elongate actuator wire is slidably disposed within the catheter lumen and has a distal end fixedly attached to the cap. The actuator wire has a distal region with a pre-formed shape such as a U-shaped bend; however the distal region is constrained within the catheter lumen to have a substantially straightened shape. A medical implant is carried within a distal portion of the catheter lumen alongside the actuator wire.

The catheter system is inserted into the patient's vasculature and is guided to a treatment site by the rounded cap. The distal region of the actuator wire is deconstrained by relative movement between the catheter and the wire to assume its pre-formed shape thereby laterally displacing the cap from the catheter distal end. With the cap no longer obstructing the path between the medical implant and the treatment site, the medical implant is ejected from the open catheter distal end.

The aforementioned and other features and advantages of the invention will become further apparent from the following detailed description of the presently preferred embodiments, read in conjunction with the accompanying drawings, which are not to scale. The detailed description and drawings are merely illustrative of the invention rather than limiting, the scope of the invention being defined by the appended claims and equivalents thereof.

DETAILED DESCRIPTION OF THE PRESENTLY PREFERRED EMBODIMENTS

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

Figure 1:
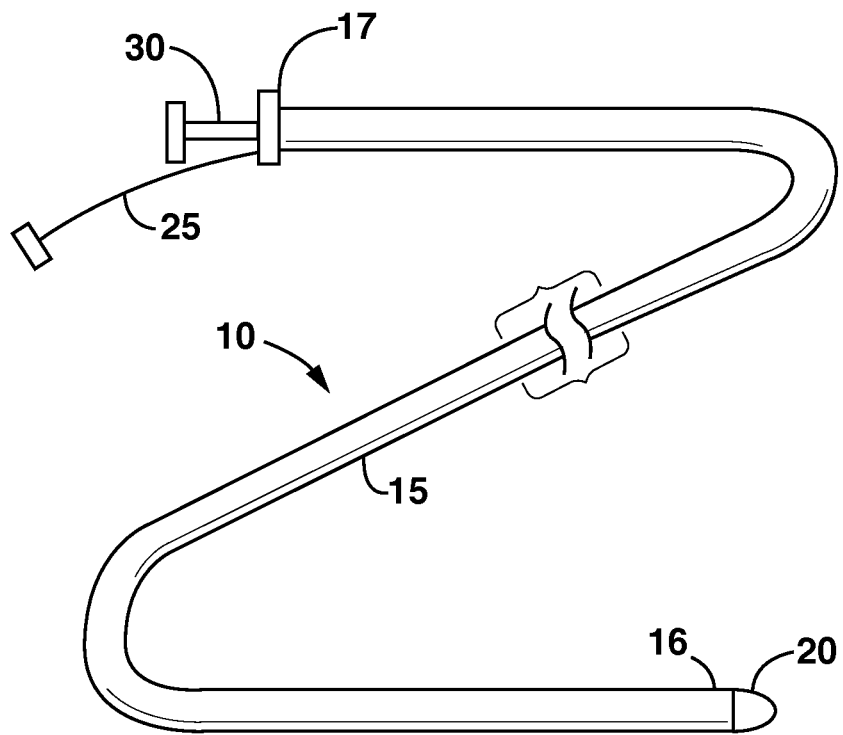
FIG. 1 illustrates a broken view of a catheter system in accordance with one aspect of the invention.

As illustrated in FIG. 1, one aspect of the present invention is catheter system 10, which includes elongate catheter 15 with rounded cap 20 removably mounted at catheter distal end 16. Actuator wire 25 and push rod 30 are shown extending from catheter proximal end 17, and will be described in further detail below.

Figure 2:
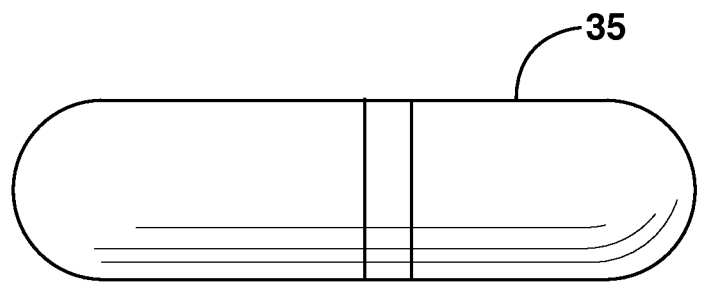
FIG. 2 illustrates a prior art medical device to be implanted.

FIG. 2 illustrates an exemplary prior art medical device 35 to be carried within catheter 15 of FIG. 1. In one embodiment, medical device 35 is a leadless pacemaker, as such devices are known in the art of pacemakers. In such embodiments, the pacemaker is typically affixed to either the septum or the apex of the right ventricle of the patient's heart. The leadless pacemaker can be delivered from a catheter either via a femoral vein approach, or a jugular vein approach depending on the patient and the clinician preference. Leadless pacemakers may include various appurtenances for fixation to and/or electrical connection with heart tissue. Such appurtenances are omitted from FIG. 2 because they are not considered part of the invention. It may be noted however, that device 35 is of a type of medical implant that intentionally lacks a lumen therethrough as could be used for catheter mounting or guidance during delivery. Medical device 35 as illustrated is also non-collapsible. Therefore, device 35 requires a delivery system having an open distal end for ejection of the implant and a lumen sized and shaped to carry the implant device to the desired treatment site.

Figure 3:
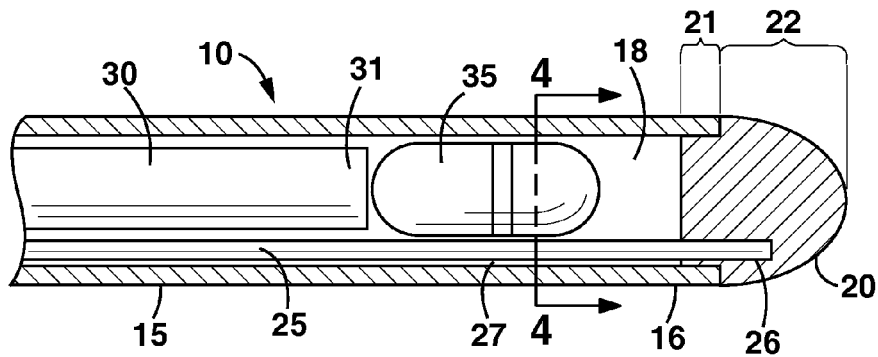
FIG. 3 illustrates a longitudinal cross section of a distal portion of a catheter system in accordance with the invention as configured for advancing through the patient's vasculature.

FIG. 3 illustrates, in a longitudinal cross sectional view, a distal region of catheter system 10 of FIG. 1. Catheter 15 has an inner surface defining lumen 18 extending from catheter proximal end 17 to catheter open distal end 16. Cap 20 is removably mounted to catheter open distal end 16. Cap proximal end 21 is sized and shaped to be slidably received in catheter lumen 18. Cap distal end 22 extends distally of catheter distal end 16 and is shaped to safely guide catheter system 10 through a patient's vasculature without catching on side branches, valves, or other obstacles along the transluminal route through the patient from the entry site to the treatment site. Cap distal end 22 may be tapered, ogival, parabolic, or another rounded shape to provide the desired bumper tip for leading catheter system 10. Cap distal end 22 is also sized and shaped to form a smooth joint with an outer surface of the catheter where it abuts catheter distal end 16.

Figure 5:
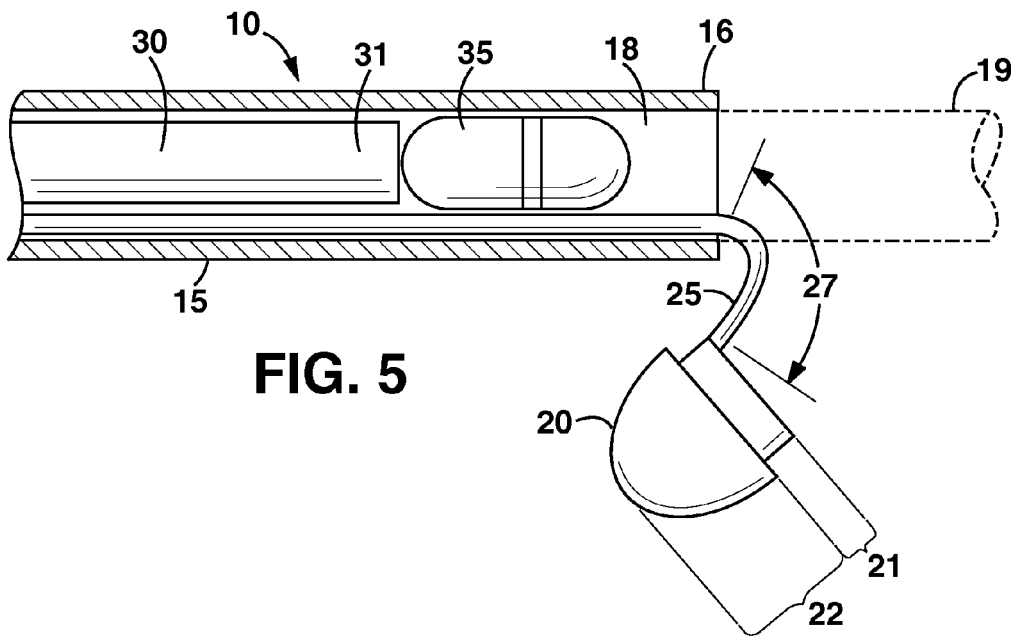
FIG. 5 illustrates a longitudinal cross section of a distal portion of the catheter system illustrated in FIG. 3, shown with the cap laterally deflected.
Figure 6:
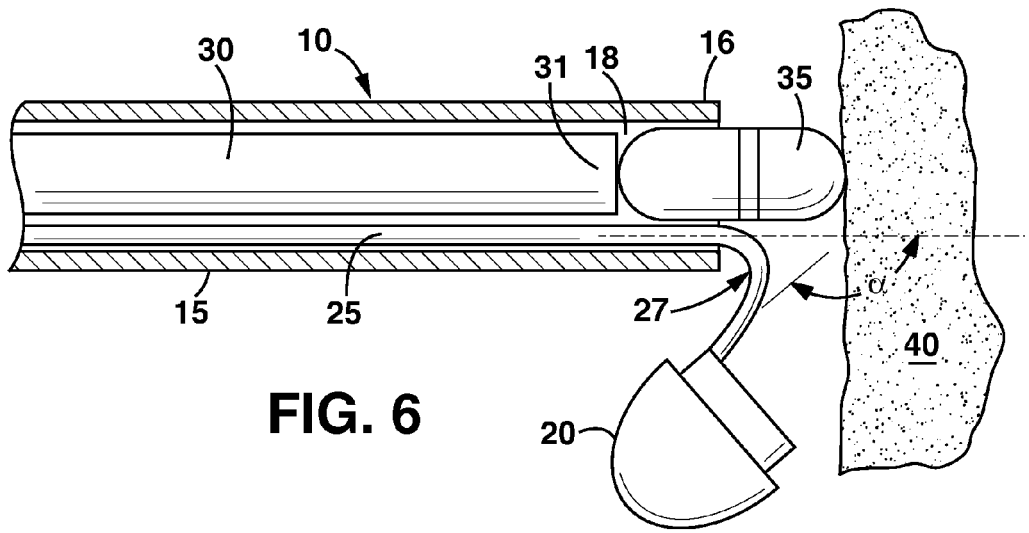
FIGS. 6 and 7 illustrate longitudinal cross sections of a distal portion of the catheter system illustrated in FIG. 3, shown while the medical device of FIG. 2 is being deployed.
Figure 7:
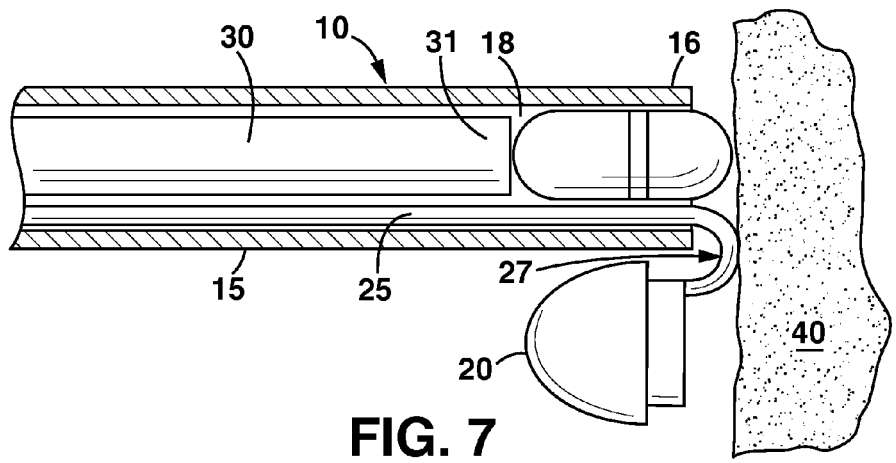

An elongate actuator wire 25 is slidably disposed within catheter lumen 18 and stretches from a wire distal end 26 fixedly attached to cap 20 to a proximal wire end extending outside of catheter proximal end 17. Referring also to FIGS. 5-7, actuator wire 25 has a distal region 27 located generally adjacent to cap 20 and having a pre-formed distal shape. As shown in FIG. 3, when wire distal region 27 is disposed and constrained in catheter lumen 18, the wire distal region has a substantially straightened shape different from the pre-formed shape that it assumes when exposed outside of the catheter lumen, as illustrated in FIGS. 5-7.

The pre-formed shape of wire distal region 27 defines a bend adapted to laterally displace cap 20 from catheter distal end 16 when it assumes the pre-formed shape. The lateral displacement of cap 20 only needs to be an amount sufficient to move cap 20 out of the path of medical implant 35 as it is exposed from catheter lumen 18. In other words, the bend of wire distal region 27 deflects cap 20 so that it does not obstruct an imaginary extension 19 of the catheter lumen 18 beyond catheter distal end 16, as shown in FIG. 5. As illustrated in FIG. 6, the bend of wire distal region 27 forms an angle α (alpha) from a straight line of approximately 150 degrees. However, the required lateral deflection of cap 20 to clear the pathway 19 for implant 35 can be achieved with an angle α ranging from about 15 degrees to about 180 degrees, or even more.

As illustrated in FIG. 7, where angle α is approximately 180 degrees, the bend of wire distal region 27 is fully U-shaped such that cap 20 is disposed alongside catheter distal end 16 and is turned around to have a reversed distal-to-proximal orientation as compared to when cap proximal end 21 is disposed within the catheter lumen 18. In the embodiment shown in FIG. 7, with cap 20 so far out of the way, catheter distal end 16 can be advanced close enough to target site tissue 40 that implant 35 can be pushed into contact with tissue 40 without implant 35 being fully exposed from catheter lumen 18. This partially deployed configuration may permit the clinician to check for correct anatomical placement of the implant 35 and/or for electrical contact with the target tissue 40, and remove or reposition catheter system 10 to achieve the desired placement of the implant 35.

Figure 4:
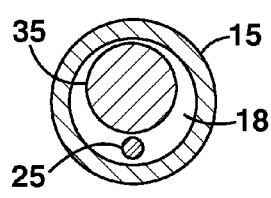
FIG. 4 illustrates a transverse cross section along line 4-4 of the catheter system illustrated in FIG. 3.

An elongate push rod 30 is slidably disposed within catheter lumen 18 and stretches from a rod distal end 31 located near catheter distal end 16 to a proximal rod end extending outside of catheter proximal end 17. Medical implant 35 may be slidably disposed distally of push rod 30 and alongside actuator wire 25 within the distal end of catheter lumen 18, as illustrated in FIGS. 3 and 4.

Figure 8:
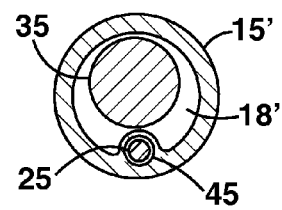
FIG. 8 illustrates a transverse cross section of a catheter system in accordance with another aspect of the invention.

An alternative embodiment, illustrated in transverse cross-section by FIG. 8, includes a second lumen 45 extending through catheter 15' separate from and parallel to first lumen 18' and adapted to slidably receiving actuator wire 25. As in the previously described embodiment, first lumen 18' is defined by an inner surface of catheter 15' and extends from the catheter proximal end to the catheter open distal end. Elongate push rod 30 is slidably disposed within catheter lumen 18' and stretches from a rod distal end located near the catheter distal end to a proximal rod end extending outside of the catheter proximal end. Medical implant 35 may be slidably disposed distally of push rod 30 within the distal end of catheter lumen 18'. The cross-sectional shape of first lumen 18' may be circular or non-circular, with the latter type being illustrated in FIG. 8. The transverse cross-sectional profile of cap proximal end 21 is sized and shaped as necessary to be slidably received in catheter lumen 18' while providing sufficient alignment of cap 20 and the catheter distal end to maintain a smooth joint where cap 20 abuts an outer surface of the catheter distal end. The size and transverse cross-sectional shape of catheter 15, 15' may vary along the length. For example, catheter 15, 15' may have a relatively larger diameter in the distal region for receiving medical implant 35. Second lumen 45 can have a rectangular shape in transverse cross-section to slidingly receive an actuator wire having a mating transverse cross-section (not shown). Rectangular or other non-circular cross-sectional shapes can aid in aligning and repositioning cap 20 on the catheter distal end after implant 35 has been deployed.

Figure 9:
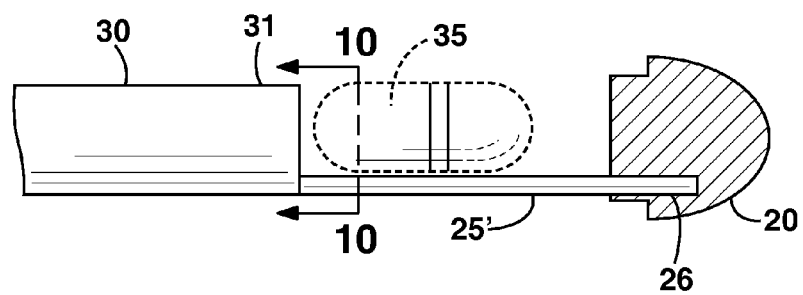
FIG. 9 illustrates a partially sectioned side view of interior components of a catheter system in accordance with yet another aspect of the invention.
Figure 10:
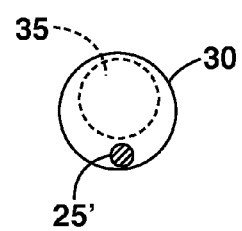
FIG. 10 illustrates a transverse cross section along line 10-10 of the interior components illustrated in FIG. 9.

FIGS. 9 and 10 illustrate the internal components of another embodiment of the catheter system wherein an elongate actuator wire 25' extends distally from push rod distal end 31 to wire distal end 26, which is fixedly attached to cap 20 as in the above embodiments. Actuator wire 25' may be integrally formed with push rod 30, or wire 25' may be constructed separately and affixed to rod distal end 31 by any means suitable for metal-to-metal or polymer-to-metal connections, depending on the materials chosen for the separate components. The connections of the proximal and distal ends of actuator wire 25' to push rod 30 and cap 20 respectively are off-center such that, when push rod 30, actuator wire 25' and cap 20 are assembled with catheter 15, medical implant 35 may be slidably disposed within the distal end of catheter lumen 18 alongside actuator wire 25' between rod distal end 33 and cap 20, similar to the embodiment illustrated in FIG. 3. During treatment with the catheter system of the alternate embodiment, relative movement between catheter 15 and push rod 30 may be used to first achieve lateral displacement of cap 20 and then to eject implant 35 from open catheter distal end 16.

The devices disclosed herein can be constructed from any suitable biocompatible material. Catheter 15, 15' may comprise a hollow tube of polyamide, polyolefin, thermoplastic polyurethane, fluoropolymer, thermoplastic elastomer of the engineering polymer family, or composites of such polymers including multiple layer constructions with or without reinforcement by, for example, braided filaments of high strength polymer or metal. Cap 20 may be formed of a polymer selected from the above examples and may be rigid or very soft to form a bumper-like tip of catheter system 10. The material of cap 20 may also be filled with a radiopacifer to enhance the image projected under x-rays, as is known to those of skill in the art of catheters. Cap 20 may, alternatively, be formed of biocompatible metal such as stainless steel.

Actuator wire 25 may be formed of spring-temper stainless steel or nitinol (TiNi) alloy having pseudo-elastic properties that result from forming stress-induced martensite (SIM). Push rod 30 may be formed of any of the above-mentioned materials to provide bending flexibility and longitudinal resistance to compression. The overall length of catheter system 10 may be selected according to the intended clinical entry site into the patient's vascular system. As non-limiting examples, the catheter may be about 90 centimeters to about 150 centimeters long, with a length of about 120 centimeters often being used. The outer diameter of the catheter may range from about 0.131 inches to 0.367 inches.

In a method of using the catheter system 10 described above, catheter 15 is inserted into a vasculature of a patient with medical implant 35 preloaded inside of the catheter distal end and cap 20 positioned to cover open catheter distal end 16. Cap proximal end 21 is disposed within open catheter distal end 16 and cap distal end 22 provides a rounded leader extending distally of catheter 15. Catheter system 10 is advanced through the patient's vasculature until it extends from the entry site to the treatment site 40.

Once the distal end of catheter system 10 reaches the region of the treatment site 40, wire distal region 27 is exposed beyond the catheter distal end 16 to permit the distal region 27 to assume its pre-formed shape thereby laterally displacing cap 20 from the catheter distal end, as illustrated in FIGS. 5-7. Exposing wire distal region 27 beyond the catheter distal end 16 is caused by relative movement between catheter 15 and actuator wire 25. For example, catheter 15 can be held stationary with respect to the patient while actuator wire 25 is advanced distally to expel cap 20 from open catheter distal end 16. Actuator wire 25 is advanced further until wire distal region 27 is extended out of open catheter distal end 16. In another example of relative movement between catheter 15 and actuator wire 25, actuator wire 25 can be held stationary with respect to the patient while catheter 15 is withdrawn proximally thereover. Exposed wire distal region 27 laterally displaces or deflects cap 20 sufficiently so that cap 20 does not obstruct the intended path 19 of medical implant 35 from open catheter distal end 16 to treatment site 40, as illustrated in FIGS. 5 and 6. Alternatively, exposed wire distal region 27 may laterally displace cap 20 so that cap 20 is disposed alongside catheter distal end 16 and is turned around to have a reversed distal-to-proximal orientation as compared to when cap proximal end 21 is disposed within the catheter lumen 18, as illustrated in FIG. 7.

Once cap 20 is out of the way, medical implant 35 may be ejected from open catheter distal end 16 by relative movement between catheter 15 and push rod 30, which is slidably disposed within catheter lumen 18. For example, catheter 15 can be held stationary with respect to the patient while push rod 30 is advanced distally to eject implant 35 from open catheter distal end 16. In another example of relative movement between catheter 15 and push rod 30, push rod 30 can be held stationary with respect to the patient while catheter 15 is withdrawn proximally thereover. The latter type of relative movement is useful when cap 20 is laterally disposed alongside and not extending substantially distal to catheter distal end 16, as illustrated in FIG. 7. In this configuration as described above, catheter distal end 16 can be advanced close enough to target site tissue 40 that implant 35 can be pushed into contact with tissue 40 without implant 35 being fully exposed from catheter lumen 18. This partially deployed configuration may permit the clinician to check for correct anatomical placement of implant 35 and/or to check for electrical contact with the target tissue 40 Because implant has not yet been ejected from open catheter distal end 16, the clinician can remove or reposition catheter system 10 to achieve the desired placement of the implant 35.

Once implant 35 has been successfully deployed, actuator wire 25 can be withdrawn back into lumen 18 to reposition cap 20 on catheter distal tend 16. Catheter system 10 can then be withdrawn from the patient.

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

What is claimed is:

1. A catheter system for intraluminal delivery of a medical implant, the system comprising:
   an elongate catheter having an inner surface defining a lumen extending from a catheter proximal end to an open catheter distal end;
   a cap disposed at the catheter distal end and having a proximal end removably disposed within the catheter lumen and a rounded distal end extending distally of the catheter distal end; and
   an elongate actuator wire slidably disposed within the catheter lumen and having a distal end fixedly attached to the cap, the actuator wire having a distal region with a pre-formed shape, the distal region having a substantially straightened shape different from the pre-formed shape when constrained within the catheter lumen and being adapted to assume its pre-formed shape when exposed distally beyond the catheter distal end, the pre-formed shape defining a bend adapted to laterally displace the cap from the catheter distal end when assuming the pre-formed shape;
   wherein at least a portion of the lumen adjacent the catheter distal end is sized and shaped to slidably receive the medical implant alongside the actuator wire.

2. The catheter system of claim 1 further comprising an elongate push rod slidably disposed within the catheter lumen and extending from a rod proximal end outside the catheter proximal end to a rod distal end located near the catheter distal end.

3. The catheter system of claim 2 further comprising the medical implant slidably disposed distally of the push rod and alongside the actuator wire within the portion of the lumen adjacent the catheter distal end.

4. The catheter system of claim 2 wherein a proximal end of the actuator wire is connected to the rod distal end.

5. The catheter system of claim 1 wherein, when the wire distal region is exposed distally beyond the catheter distal end, the laterally displaced cap does not obstruct an imaginary extension of the catheter lumen beyond the catheter distal end.

6. The catheter system of claim 1 wherein, when the wire distal region is exposed distally beyond the catheter distal end, the bend defined by the pre-formed shape forms an angle from a straight line of between about 15 degrees and about 180 degrees.

7. The catheter system of claim 1 wherein, when the wire distal region is exposed distally beyond the catheter distal end, the bend defined by the pre-formed shape forms a U-shape such that the cap is disposed alongside the catheter distal end and the cap has a reversed distal-to-proximal orientation as compared to when the cap proximal end is disposed within the catheter lumen.

8. The catheter system of claim 1 wherein a proximal end of the actuator wire extends outside the catheter proximal end.

9. The catheter system of claim 1 wherein the rounded distal end of the cap is sized and shaped to form a smooth joint with an outer surface of the catheter where it abuts the distal end of the catheter.

10. A method for delivering a medical implant to a treatment site in a patient, the method comprising:
   inserting a catheter system into a vasculature in the patient, the system including:
      an elongate catheter having an inner surface defining a lumen extending from a catheter proximal end to an open catheter distal end;
      a cap removably disposed at the catheter distal end and having a proximal end disposed within the catheter lumen and an rounded distal end extending distally of the catheter distal end;
      an elongate actuator wire slidably disposed within the catheter lumen and having a distal end fixedly attached to the cap, the actuator wire having a distal region with a pre-formed shape, the distal region being constrained within the catheter lumen to have a substantially straightened shape different from the pre-formed shape; and
      a medical implant slidably disposed alongside the actuator wire within a portion of the lumen adjacent the catheter distal end;
   advancing the catheter through the vasculature to a location near the treatment site;
   causing relative movement between the actuator wire and the catheter to expose the wire distal region beyond the catheter distal end and to permit the distal region to assume its pre-formed shape thereby laterally displacing the cap from the catheter distal end; and
   ejecting the medical implant from the open catheter distal end.

11. The method of claim 10 wherein causing relative movement between the actuator wire and the catheter comprises holding the actuator wire stationary with respect to the patient while withdrawing the catheter proximally over the actuator wire.

12. The method of claim 10 wherein the catheter system further includes an elongate push rod slidably disposed within the catheter lumen and extending from a rod proximal end outside the catheter proximal end to a rod distal end abutting the medical implant;
   wherein ejecting the medical implant comprises causing relative movement between the push rod and the catheter to expose the medical implant.

13. The method of claim 12 wherein causing relative movement between the push rod and the catheter comprises holding the push rod stationary with respect to the patient while withdrawing the catheter proximally over the actuator wire.

14. The method of claim 10 wherein the pre-formed shape of the wire distal region comprises a U-shape such that when the distal region is permitted to assume its pre-formed shape the cap is disposed alongside the catheter distal end and the cap has a reversed distal-to-proximal orientation as compared to when the cap proximal end is disposed within the catheter lumen.

15. The method of claim 14 wherein, when the cap is disposed alongside the catheter distal end, the catheter is farther advanced through the vasculature until the open catheter distal end abuts the treatment site.

16. The method of claim 12 wherein a proximal end of the actuator wire is connected to the rod distal end.

17. The method of claim 16 wherein relative movement between the push rod and the catheter also causes corresponding relative movement between the actuator wire and the catheter.

* * * * *